United States Patent
Bottasso et al.

(10) Patent No.: US 7,442,374 B2
(45) Date of Patent: Oct. 28, 2008

(54) COMPOSITION FOR INCREASING THE SURVIVAL TO SLAUGHTER RATE OF PIGLETS

(75) Inventors: Oscar Adelmo Bottasso, Provincia de Santa Fe (AR); Graham McIntyre, Kent (GB); Cynthia Ann Stanford, Kent (GB); John Lawson Stanford, Kent (GB)

(73) Assignee: UCL BioMedica Plc, London (GB)

( * ) Notice: Subject to any disclaimer, the term of this patent is extended or adjusted under 35 U.S.C. 154(b) by 0 days.

(21) Appl. No.: 10/893,524

(22) Filed: Jul. 19, 2004

(65) Prior Publication Data
US 2006/0013830 A1  Jan. 19, 2006

(51) Int. Cl.
*A61K 39/00* (2006.01)
*A61K 39/116* (2006.01)
*A01N 63/00* (2006.01)
*C12Q 1/70* (2006.01)
*C12Q 1/68* (2006.01)

(52) U.S. Cl. ............... 424/184.1; 424/203.1; 424/93.4; 435/5; 435/6

(58) Field of Classification Search .............. 435/6, 435/5; 424/203.1, 93.4, 184.1
See application file for complete search history.

(56) References Cited

U.S. PATENT DOCUMENTS

2006/0134136 A1* 6/2006 McIntyre et al. ......... 424/203.1

FOREIGN PATENT DOCUMENTS

| WO | WO 02/32455 | 4/2002 |
| WO | WO 2004/022093 | 3/2004 |
| WO | WO 2005/049056 | 6/2005 |

OTHER PUBLICATIONS

Possible treatment options for PMWS/PDNS, Veterinary Record, 2000; 146(21): 619-20.*
DuPont Animal Health Solutions, http://www.antecint.co.uk/main/pdns.htm.*
Ellis, R., New Technologies for Making Vaccines, Vaccines (text book) 1988: 568-575.*
Boslego, J. et al, Gonorrhea Vaccines (chapter 17); 211-223.*
DuPont Animal Health Solutions, http://www.antecint.co.uk/main/pdns.htm, Aug. 3, 2005.*
Ellis, R., New Technologies for Making Vaccines, Vaccines (text book) 1988: 568-575.*
Boslego, J. et al, Gonorrhea Vaccines (chapter 17); 211-223.*
Pig & Poultry Fair poster, "Novel Growth Promoter." Stoneleigh Park, UK, May 12-13, 2004.

* cited by examiner

*Primary Examiner*—Robert A. Zeman
*Assistant Examiner*—Lakia J Tongue
(74) *Attorney, Agent, or Firm*—Steptoe & Johnson LLP

(57) ABSTRACT

This invention relates to a method for treating or preventing (including immunising against) post-wearing multisystemic wasting syndrome (PMWS) and/or porcine dermatitis and nephropathy syndrome (PDNS) in a subject comprising administering an effective amount of a pharmaceutical composition or immune modulator composition comprising a whole cell of a bacterium from one or more of the genera *Rhodococcus, Gordonia, Nocardia, Dietzia, Tsukamurella* and *Nocardioides*, to said subject. In addition the method relates to the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of post-wearing multisystemic wasting syndrome (PMWS) and/or porcine dermatitis and nephropathy syndrome (PDNS).

5 Claims, 1 Drawing Sheet

Model

Placebo group

*R.coprophilus* group

COMPOSITION FOR INCREASING THE SURVIVAL TO SLAUGHTER RATE OF PIGLETS

FIELD OF INVENTION

The present invention relates to an immune modulator composition and/or pharmaceutical composition which is effective in the treatment and/or prevention of post weaning multisystemic wasting syndrome and/or porcine dermatitis and nephropathy.

BACKGROUND TO THE INVENTION

Post-weaning multisystemic wasting syndrome (PMWS) affects piglets post-weaning from 4 to 16 weeks of age (15-50 kg). Typically PMWS affects piglets one to two weeks after weaning and is very different from the wasting/poor weaner who fails to eat or drink adequately after weaning. PMWS piglets are weaners which have started to grow and then collapse quickly and often have an extremely poor response to antibiotics.

Porcine dermatitis and nephropathy syndrome (PDNS) affects pigs from 8 to 18 weeks of age and the most obvious signs are red-purple blotches on the skin, which become brown and crusted after a few days. Pigs are lethargic and may have swollen legs resulting from their nephropathy. This syndrome, also, responds poorly to antibiotics.

The causal agents of both PMWS and PDNS are at present unknown. The most likely suspect in both syndromes is a pig circovirus "type II" which is antigenically distinct from widely distributed normal non-pathogenic pig circovirus "type I". Circovirus II (PCV II) has been identified on UK farms serologically. PDNS, which is thought to be an immune complex mediated disease, may also involve bacteria in its aetiology, though the part that they play is not clear.

PMWS is a problem which is recognised world-wide. PMWS was first reported in Canada in 1991, with reported incidents following in France (1995); USA (1996); Spain (1997); Austria, Denmark, Germany, Ireland, Italy, Netherlands and Northern Ireland (1998); Great Britain, Hungary, Japan, Korea, Portugal and Taiwan (1999); Poland (2000); Mexico (2001); and New Zealand (2003).

PDNS was first described in the UK in 1993 as a sporadic condition but since that time it has become increasingly associated with herds affected by PMWS, and has been reported all over the world.

With PMWS and PDNS the mortality rate is very high. The clinical characteristics of both PMWS and PDNS syndromes include an initial high fever (40-42° C.). Pigs with PMWS develop listlessness; very rapid wasting; development of a hairy coat and runted appearance. In addition, the lymph nodes may be palpable as they are grossly enlarged. With either syndrome, some pigs may also develop a slight cough and difficulty breathing.

To date, no effective treatments of or vaccines for PMWS or PDNS are available. As a general guide the following regimes have been used in order to attempt to combat both syndromes: changing of the herd to all-in or all-out protocols; age segregation; providing pigs with a good environment to limit effects of secondary infection; separating weaners that show signs of the disease to reduce the level of the disease in the pen; good gilt introduction protocols to ensure gilts are well acclimatised before entry into the main unit; and minimising cross-fostering.

These regimes, however, are limited in their effectiveness. An aim of the present invention is to more effectively protect against and/or treat and/or reduce the level of occurrence of both PMWS and/or PDNS.

SUMMARY OF THE INVENTION

A seminal finding of the present invention is that post-weaning multisystemic wasting syndrome (PMWS) and/or porcine dermatitis and nephropathy syndrome (PDNS) can be treated and/or prevented and/or reduced by administration of a whole cell of a bacterium from the genera *Rhodococcus, Gordonia, Nocardia, Dietzia, Tsukamurella* and *Nocardioides* or an immune modulator composition and/or pharmaceutical composition comprising a whole cell of a bacterium from the genera *Rhodococcus, Gordonia, Nocardia, Dietzia, Tsukamurella* and *Nocardioides*.

DETAILED ASPECTS OF THE INVENTION

In one aspect, the present invention provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of post-weaning multisystemic wasting syndrome (PMWS) and/or porcine dermatitis and nephropathy syndrome (PDNS).

In another aspect, the present invention provides the use of a whole cell of a bacterium from the genera *Rhodococcus, Gordonia, Nocardia, Dietzia, Tsukamurella* and *Nocardioides*, in the manufacture of a medicament for the treatment or prevention of post-weaning multisystemic wasting syndrome (PMWS) and/or porcine dermatitis and nephropathy syndrome (PDNS).

In a further aspect, the present invention provides a method for treating or preventing post-weaning multisystemic wasting syndrome (PMWS) and/or porcine dermatitis and nephropathy syndrome (PDNS) in a subject comprising administering an effective amount of a pharmaceutical composition or immune modulator composition comprising a whole cell of a bacterium from the genera *Rhodococcus, Gordonia, Nocardia, Dietzia, Tsukamurella* and *Nocardioides*, to a subject.

Suitably, the effective amount of the pharmaceutical composition and/or immune modulator composition may be administered as a single dose. Alternatively, the effective amount of the pharmaceutical composition and/or immune modulator composition may be administered in multiple (repeat) doses, for example two or more, three or more, four or more, five or more, six or more, ten or more, twenty or more repeat doses.

In another aspect, the present invention provides a method for protecting, including immunising, a subject from post-weaning multisystemic wasting syndrome (PMWS) and/or porcine dermatitis and nephropathy syndrome (PDNS) comprising administering a pharmaceutical composition or immune modulator composition comprising a whole cell of a bacterium from the genera *Rhodococcus, Gordonia, Nocardia, Dietzia, Tsukamurella* and *Nocardioides*, to the subject.

Preferably, the pharmaceutical composition or immune modulator composition is administered in early life, such as within the first 3 months of birth, preferably within the first 3 weeks of birth.

The term "protected" as used herein means that the subject is less susceptible to the disease/disorder as compared with a subject not treated or administered with the compositions according to the present invention and/or that the subject is more able to counter or overcome the disease/disorder as compared with a subject not treated or administered with the compositions according to the present invention.

The term "immune modulator" as used herein means a substance which modulates a cellular immune system of a subject. The term "immune modulator" as used herein includes a vaccine.

The phrase "cellular immune system" as used herein, includes a cell-mediated immune response which depends upon the presence of T-lymphocytes (and optionally antigen presenting cells). The term "T-lymphocytes" includes cytotoxic T-lymphocytes, help T cells, suppressor T cells and regulatory T cells.

The term "whole cell", as used herein, means a bacterium which is intact, or substantially intact. In particular, the term "intact" as used herein means a bacterium which is comprised of all of the components present in a whole cell, particularly a whole, viable cell, and/or a bacterium which has not been specifically treated to remove one or more components from it. By the term "substantially intact" as used herein it is meant that although the isolation and/or purification process used in obtaining the bacterium may result in, for example, a slight modification to the cell and/or in the removal of one or more of the components of the cell, the degree to which such a modification and/or removal occurs is insignificant. In particular, a substantially intact cell according to the present invention has not been specifically treated to remove one or more components from it.

WO2004/022093 and UK application number 0404102.6 (both of which references are incorporated herein by reference) disclose an immune modulator composition or a pharmaceutical composition comprising a whole cell of a bacterium from the genera *Rhodococcus, Gordonia, Nocardia, Dietzia, Tsukamurella* and *Nocardioides*. However, neither of these documents teaches or suggests the use of such an immune modulator composition or pharmaceutical composition for the treatment and/or prevention of the two clinical syndromes PMWS or PDNS.

Suitably, the immune modulator composition or pharmaceutical composition used herein may comprise a pharmaceutically acceptable carrier, diluent or excipient.

Suitably, the immune modulator composition and/or pharmaceutical composition may comprise more than one whole cell, and more preferably comprises a plurality of whole cells.

In one aspect, the immune modulator composition and/or a pharmaceutical composition comprising the whole cell of a bacterium from the genera *Rhodococcus, Gordonia, Nocardia, Dietzia, Tsukamurella* and *Nocardioides* may further comprise at least one, or at least one further, antigen or antigenic determinant.

Suitably, the antigen or antigenic determinant may be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine), *Mycobacterium vaccae*, or part thereof (as taught in GB0025694.1) and a generic plasmodium antigen, for example a malaria parasite antigen.

Suitably, the immune modulator composition and/or pharmaceutical composition may comprise two or more such antigens or antigenic determinants.

The pharmaceutical composition and/or an immune modulator composition used in accordance with the present invention may be co-administered to the subject with an antigen or antigenic determinant.

When the composition is co-administered with an antigen or antigenic determinant in accordance with the present invention the antigen or antigenic determinant may suitably be an antigen or antigenic determinant from one or more of the following: porcine circavirus type II, other porcine viruses, bacteria of the genera *Streptococcus, Haemophilus, Salmonella, Mycoplasma, Actinobacillus, Bordetella* and *Pasteurella* that have been associated with either syndrome, BCG (*bacillus* of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine), *Mycobacterium vaccae*, or part thereof (as taught in GB0025694.1) and a generic plasmodium antigen, for example a malaria parasite antigen. Suitably two or more, or three or more, of such antigens or antigenic determinants may be co-administered with a pharmaceutical composition or an immune modulator composition according to the present invention.

The immune modulator composition used in accordance with the present invention may be a vaccine. The vaccine may be a prophylactic vaccine or a therapeutic vaccine.

Suitably, the composition for use in accordance with the present invention may comprise two or more, or three or more, bacteria from any one of the genera *Rhodococcus, Gordonia, Nocardia, Dietzia, Tsukamurella* and *Nocardioides*.

Preferably, the bacteria for use in accordance with the present invention are any species from any of the genera *Rhodococcus, Gordonia, Nocardia, Diezia, Tsukamurella* and *Nocardioides*, such as *Gordonia bronchialis, G. amarae, G. sputti, G. terrae, Nocardia asteroides, Dietzia maris, Tsukamurella paurometabola, Rhodococcus ruber, Rhodococcus rhodnii, R. coprophilus, R. opacus, R. erythopolis, Nocardicides albus* and *Tsukamurella inchonensis* for example. Suitably, the species used from each particular genus are ones which can be grown on medium, which is a low, preferably, non-, antigenic medium. By way of example only, a suitable non-antigenic medium is Sauton's medium.

More preferably, the bacteria for use in accordance with the present invention are from the genus *Rhodococcus* including *Rhodococcus ruber* (previously known as *Nocardia rubra*), *Rhodococcus rhodocrous, Rhodococcus rhodnii, Rhodococcus coprophilus, Rhodococcus opacus, Rhodococcus erythopolis*.

More preferably, the bacteria for use in accordance with the present invention is *Rhodococcus coprophilus*.

The term "subject", as used herein, means an animal. Preferably, the subject is a mammal, bird, fish or crustacean including for example livestock and humans. Preferably, the subject referred to herein is a pig or a piglet. PMWS and PDNS are specifically diseases of pigs, although other species may be subject to related syndromes. It is intended that the present invention could be used in the treatment of related syndromes in subjects other than pigs. Hence, the present invention is effective for the treatment and/or prevention and/or reduction of PMWS or PDNS in pigs (including piglets). However, should this syndrome or a similar syndrome be identified in another subject, such as a different livestock, it is envisaged that the immune modulator composition and/or pharmaceutical composition taught herein would be effective to treat and/or prevent such a syndrome in other subjects, such as in other livestock. The term "livestock" as used herein refers to any farmed animal. Preferably, livestock is one or more of poultry, pigs (including piglets), sheep (including lambs), cows or bulls (including calves), fish and crustaceans. More preferably, livestock means pigs—including piglets.

The circa viruses and agents probably associated with PDNS and PMWS are commensal or latent viruses carried by the majority of pigs and usually only erupt and produce a diseased state under certain circumstances, such as an altered immune status. It is therefore envisaged that the immune modulator composition and/or pharmaceutical composition according to the present invention may be used to treat and/or prevent other diseases and/or disorders caused by similar latent viruses and/or to treat and/or prevent other idiopathic eruptions.

Preferably, the bacterium according to the present invention is killed prior to use. Preferably, the bacterium according to the present invention is killed by heat-treatment thereof, for example, heat-treatment in an autoclave at 121° C. for 15 minutes. Other suitable treatments for killing the bacterium may include ultraviolet or ionising radiation or treatment with chemicals such as phenol, alcohol or formalin.

Preferably, the bacterium according to the present invention is purified and/or isolated.

Preferably, the bacterium according to the present invention is suspended in water or buffered saline, suitably borate buffered at pH 8.

Preferably, the pharmaceutical composition or immune modulator composition is administered (for the first time if more than one administration is to be made) after the livestock has suckled for the first time. In particular, for some applications it may be important to allow the infant to take in and/or digest the parents colostrum prior to administering the pharmaceutical composition or immune modulator composition or prior to administering the first dose of the pharmaceutical composition or immune modulator composition (where there is more than one dose). For the avoidance of doubt, for some applications the first administration should not be give on the actual day of birth (0-day). For some embodiments, the first administration of the pharmaceutical composition or immune modulator composition should be give between about 1-4 days post-birth, preferably 1-3 days post-birth, more preferably 1-2 days post-birth, more preferably 2-3 days post-birth. Subsequent administrations may be given 7 days and/or 14 days and/or 8-12 weeks after the first injection.

Vaccines

The preparation of vaccines which contain one or more substances as an active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the active ingredient(s) encapsulated in liposomes. The active ingredients are often mixed with excipients which are pharmaceutically acceptable and compatible with the active ingredient. Suitable excipients are, for example, water, saline, dextrose, glycerol, ethanol, or the like and combinations thereof. Alternatively, the vaccine may be prepared, for example, to be orally ingested and/or capable of inhalation.

In addition, if desired, the vaccine may contain minor amounts of auxiliary substances such as wetting or emulsifying agents and pH buffering agents.

Administration

Typically, a physician will determine the actual dosage of a vaccine, immune modulator composition and pharmaceutical composition which will be most suitable for an individual subject and it will vary with the age, weight and response of the particular subject. The dosages below are exemplary of the average case. There can, of course, be individual instances where higher or lower dosage ranges are merited.

Preferably, the actual dosage that is used results in minimal toxicity to the subject.

The compositions of the present invention may be administered by direct injection. The composition may be formulated for parenteral, mucosal, intramuscular, intravenous, subcutaneous, intraocular, intradermal or transdermal administration.

Suitably, the composition according to the present invention may be administered at a dose of $10^3$-$10^{11}$ organisms, preferably $10^4$-$10^{10}$ organisms, more preferably $10^6$-10-5× $10^9$ organisms, and even more preferably $10^6$-$10^9$ organisms. Typically, the composition according to the present invention may be administered at a dose of $10^8$-$10^9$ bacteria for human and animal use.

If the compositions of the present invention are to be administrated as immune enhancers, then $10^3$-$10^{11}$ organisms per dose, preferably $10^4$-$10^{10}$ organisms per dose, more preferably $10^6$-10-5×$10^9$ organisms per dose, and even more preferably $10^6$-$10^9$ organisms per dose, and even more preferably, $10^8$-$10^9$ bacteria per dose for human and animal use may be administered at regular intervals.

As will be readily appreciated by a skilled person the dosage administered will be dependent upon the organism to which the dose is being administered.

The term "administered" includes delivery by delivery mechanisms including injection, lipid mediated transfection, liposomes, immunoliposomes, lipofectin, cationic facial amphiphiles (CFAs) and combinations thereof, or even viral delivery. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular, intradermal or subcutaneous route.

The term "co-administered" means that the site and time of administration of each of the adjuvants(s), antigen(s) and/or antigenic determinant(s) of the present invention are such that the necessary modulation of the immune system is achieved. Thus, whilst the antigen(s) and adjuvant(s) may be administered at the same moment in time and at the same site, there may be advantages in administering the antigen(s) and/or antigenic determinant(s) at a different time and to a different site from the adjuvant(s). The antigen(s) and/or antigenic determinant(s) and adjuvant(s) may even be delivered in the same delivery vehicle—and the antigen(s) and/or antigenic determinant(s) and adjuvant(s) may be coupled and/or uncoupled and/or genetically coupled and/or uncoupled. By way of example only, the immune modulator composition according to the present invention may be administered before, at the same time or post administration of one or more antigens or further antigens.

The antigen, antigenic determinant, peptide or homologue or mimetic thereof may be administered separately or co-administered to the host subject as a single dose or in multiple doses.

The immune modulator composition and/or pharmaceutical composition for use in accordance with the invention may be administered by a number of different routes such as injection (which includes parenteral, subcutaneous, intradermal and intramuscular injection) intranasal, mucosal, oral, intra-vaginal, urethral or ocular administration.

Preferably, in the present invention, administration is by injection. More preferably the injection is intradermal.

Preferably, in the present invention, administration is by an orally acceptable composition.

For vaccination the composition can be provided in 0.1 to 0.2 ml of aqueous solution, preferably buffered physiological saline, and administered parenterally, for example by intradermal inoculation. The vaccine according to the invention is preferably injected intradermally. Slight swelling and redness, sometimes also itching may be found at the injection site. The mode of administration, the dose and the number of administrations can be optimised by those skilled in the art in a known manner.

Antigens

As used herein, an "antigen" means an entity which, when introduced into an immunocompetent host, modifies the production of a specific antibody or antibodies that can combine with the entity, and/or modifies the relevant T-helper cell response, such as Th2 and/or Th1. The antigen may be a pure substance, a mixture of substances or soluble or particulate material (including cells or cell fragments or cell sonicate). In this sense, the term includes any suitable antigenic determinant, cross reacting antigen, alloantigen, xenoantigen, tolerogen, allergen, hapten, and immunogen, or parts thereof, as well as any combination thereof, and these terms are used interchangeably throughout the text.

The term "antigenic determinant or epitope" as used herein refers to a site on an antigen which is recognised by an antibody or T-cell receptor, or is responsible for evoking the T-helper cell response. Preferably it is a short peptide derived from or as part of a protein antigen. However the term is also intended to include glycopeptides and carbohydrate epitopes. The term also includes modified sequences of amino acids or carbohydrates which stimulate responses which recognise the whole organism.

It is advantageous if the antigenic determinant is an antigenic determinant of the infectious agent which causes the infectious disease.

A "preventative" or "prophylactic" vaccine is a vaccine which is administered to naive individuals to prevent development of a condition, such as by stimulating protective immunity.

A "therapeutic" vaccine is a vaccine which is administered to individuals with an existing condition to reduce or minimise the condition or to abrogate the immunopathological consequences of the condition.

Adjuvants

The term 'adjuvant' as used herein means an entity capable of augmenting or participating in the influencing of an immune response. An adjuvant is any substance or mixture of substances that assists, increases, downregulates, modifies or diversifies the immune response to an antigen.

The immune modulator composition and/or pharmaceutical composition according to the present invention may comprise one or more adjuvants which enhance the effectiveness of the immune modulator composition and/or pharmaceutical compositions. Examples of additional adjuvants which, may be effective include but are not limited to: aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis, Mycobacterium vaccae*, polyribonucleotides, sodium alginate, lanolin, lysolecithin, vitamin A, interleukins such as interleukin 2 and interleukin-12, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Only aluminium hydroxide is approved for human use. Some of the other adjuvants, such as *M. vaccae* for example, have been approved for clinical trials.

Suitably, the adjuvant may be a whole cell of a bacterium from any one of the genera *Rhodococcus, Gordonia, Nocardia, Dietzia, Tsukamurella* and *Nocardioides*.

In the art, it is known that DNA vaccines, which are essentially DNA sequences attached to gold particles and which are fired into the skin by a helium gun, are efficient vaccine delivery systems. Unlike conventional vaccines, these DNA vaccines do not require a traditional adjuvant component. In accordance with a further aspect of the present invention, the immune modulator composition as defined herein may suitably be used in conjunction with such DNA vaccines to augment or participate in the influencing of the immune response.

Pharmaceutical Compositions

The present invention also provides a pharmaceutical composition comprising a therapeutically effective amount of a whole cell of a bacterium from the genera *Rhodococcus, Gordonia, Nocardia, Dietzia, Tsukamurella* and *Nocardioides* and optionally a pharmaceutically acceptable carrier, diluent or excipients (including combinations thereof).

The pharmaceutical composition may comprise two components—a first component comprising an antigen and a second component comprising an adjuvant thereof. The first and second component may be delivered sequentially, simultaneously or together, and even by different administration routes.

Suitably, the antigen may even be engendered within the host tissues as part of a disease process. Thus, antigen may originate from a bacterial, host or parasitic invasion, or may be a substance released from the tissues such as a stress protein, equivalent to the heat-shock proteins of bacteria or a tumour antigen.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular, intradermal or subcutaneous route. Alternatively, the formulation may be designed to be delivered by both routes.

Preferably in the present invention the formulation is of injectable form. More preferably the formulation is intradermally injected.

Preferably in the present invention the formulation is an orally acceptable composition.

Where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly, intradermally or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner, or the compositions may be administered by incorporation into the food and/or feed of the subject.

Pharmaceutical Combinations

The agent of the present invention may be administered with one or more other pharmaceutically active substances. By way of example, the present invention covers the simultaneous, or sequential treatments with an immune modulator composition and/or pharmaceutical composition according to the present invention, and one or more steroids, analgesics, antivirals, interleukins such as IL-2, or other pharmaceutically active substance(s).

It will be understood that these regimes include the administration of the substances sequentially, simultaneously or together.

Immune Enhancer

The term "immune enhancer" as used herein means one or more bacteria either isolated or in culture which when administered to a subject benefit the health of that subject. Preferably, this benefit is achieved by the modification of the cellular immune response of the subject.

In accordance with the present invention, immune enhancers may be used for the treatment of PMWS or PDNS.

The immune enhancers may be administered by consumption in specially designed food or in animal feeds, for example pig animal feeds supplemented with the bacteria of the present invention.

The immune enhancers may also be administered by other routes—such as direct injection.

Preferably, the bacteria are killed so as to avoid the difficulties of maintaining live products and/or to expose immunologically active substances often hidden in live bacteria.

Identifying a Bacterium that Modulates a Cellular Immune Response

In another aspect, the present invention relates to a method for identifying one or more whole cells of bacteria from the genera *Rhodococcus, Gordonia, Nocardia, Dietzia, Tsukamurella* and *Nocardioides* that can treat and/or prevent PMWS or PDNS comprising the steps of: (a) administering a first group of test animals with an immunostimulant; (b) administering a second group of test animals with an immunostimulant mixed with a bacterium; (c) measuring the number or occurrences of and/or severity of PMWS or PDNS in each of the test animals; and (d) comparing the results in each of the groups of test animals, wherein, a lower occurrence of and/or severity of PMWS or PDNS from the immunostimulant mixed with a bacterium in comparison to the immunostimulant alone is indicative of a bacterium suitable for use in accordance with the present invention.

As used herein, the term "test animal" refers to any animal that elicits a cellular immune response to the immunostimulant. Preferably, the test animal(s) is a mammal.

Preferably, the bacterium modifies the T helper cell response. Suitably, the bacterium may modify the T helper cell response by decreasing the Th1 and Th2 response. Suitably, the bacterium may modify the T helper cell response by increasing the Th1 response and decreasing the Th2 response. Suitably, the bacterium may modify the T helper cell response by increasing the Th1 response without affecting the Th2 response.

Preferably, the immunostimulant will have a known Th1 and Th2 response. For example, with the immunostimulant BCG the reaction is usually largest at 24 h when it is an indicator of the Th1 response; the reaction at 48 h is usually less and includes a Th2 contribution. It is known that BCG predominantly stimulates a Th1 response.

By use of such immunostimulants it may be possible to determine the Th1/Th2 response of a test bacterium and, thus, it may be possible to identify one or more bacteria which have a desired Th1/Th2 response to treat and/or prevent a particular disease and/or disorder.

Preferably, the cellular immune response is measured using the tuberculin skin test. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

Vaccination with an immunostimulant—such as BCG—induces a response to skin-testing with tuberculin (a soluble preparation of Tubercle bacilli), when tested later. The local reaction is measured at various intervals, for example, 24 hours, 48 hours and 72 hours after injection of tuberculin. Briefly, an immunostimulant (e.g. BCG) is used that induces a positive immune response to tuberculin. In the test animal, the tuberculin skin test is preferably carried out on the foot pad. In a predominant Th1 reaction the positive foot pad immune response is usually maximal at 24 hours and diminishes at 48 hours. However, as the Th2 reactivity increases then the 48 hour positive foot pad immune response increases and can even exceed the foot pad immune response at 24 hour. Thus, the assay can be used to assess whether or not the introduction of an immune modulator composition according to the present invention modulates the cellular immune response.

Preferably, the immunostimulant is BCG.

The invention will now be further described by way of Examples and Figures, which are meant to serve to assist one of ordinary skill in the art in carrying out the invention and are not intended in any way to limit the scope of the invention.

EXAMPLES

Prevention Experiment

Groups of 1 to 3 day old piglets are injected into the skin of the neck with 0.1 ml of a suspension of 10 mg/ml of the selected immune modulator, e.g. *Rhodococcus coprophilus*, or with saline as a control. This is repeated 7 and/or 14 days later, and when animals are 8-12 weeks old, making sure that the same preparation is applied to the same pigs on each occasion. Pigs are then followed until they are 20 weeks of age, with regular checks for the appearance of the signs of either PMWS or PDNS.

Up to 10% of pigs (normally 3-5%) receiving injections of placebo develop either PMWS or PDNS within this timeframe in comparison with less than 1% of immune-modulated pigs developing the syndromes.

Figure 1:
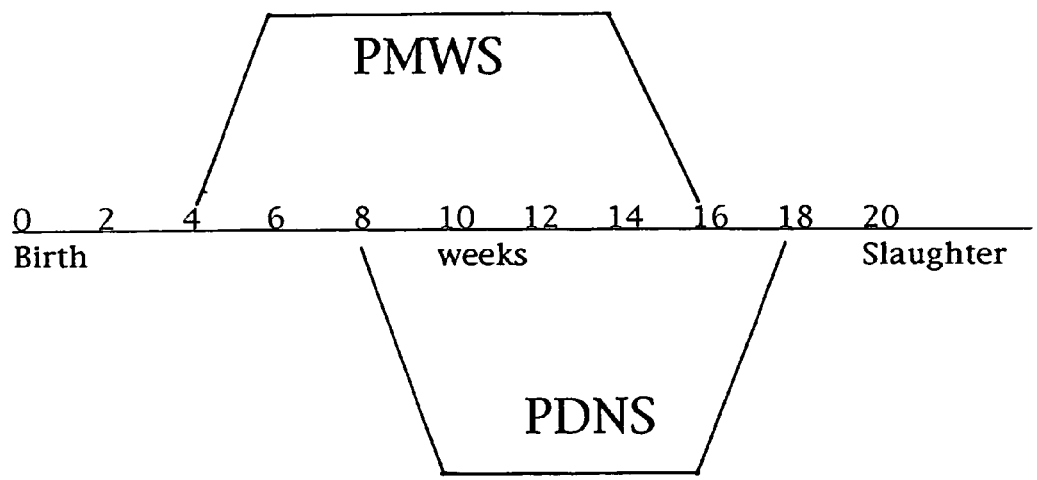
FIG. 1 shows the timings for the occurrence both PMWS and PDNS during the lifespan of piglets/pigs together with the results of treating piglets with an immune modulator comprising *R. coprophilus* compared with a placebo.
Figure 1:
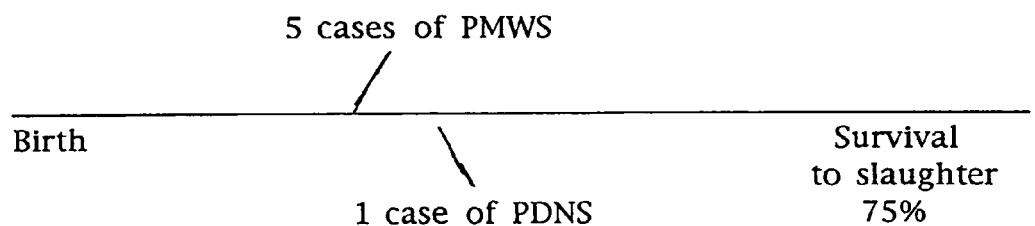
Figure 1:
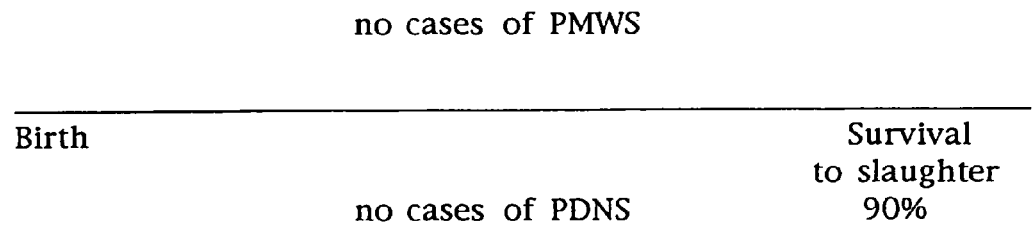

The results of 1 particular experiment can be seen in FIG. 1. The timings for both PMWS and PDNS are shown in FIG. 1 and the results obtained showed a 15% increase in the survival to slaughter rate of pigs treated with *R. coprophilus* as an immune modulator compared to pigs treated with placebo.

Treatment Experiment

Animals showing the earliest signs of PMWS or PDNS will be randomised to receive either a course of immune modulator, or of placebo. Injections will be given immediately the diagnosis is suspected, and repeated at 2 weekly intervals until the animal recovers or dies. Samples of blood and biopsies of tissues will be sampled from each animal for confirmation of the suspected diagnosis. Groups of 10 animals with confirmed PMWS or PDNS will be allocated to each treatment group.

Preliminary investigations suggest that pigs treated with the immune modulator will increase the survival to slaughter rate of pigs compared with pigs treated with the placebo.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for increasing the survival to slaughter rate in a pig comprising administering an effective amount of a composition comprising a whole cell of *Rhodococcus coprophilus* to said pig.

2. A method according to claim 1 wherein the composition is administered to a piglet.

3. A method according to claim 1 wherein the *Rhodococcus coprophilus* is killed.

4. A method according claim 1 wherein the composition is administered for the first time after the pig has taken in or digested colostrum.

5. A method according claim 2 wherein the composition is administered for the first time after the piglet has taken in or digested colostrum.

* * * * *